(12) United States Patent
Gonzalez et al.

(10) Patent No.: US 10,745,633 B2
(45) Date of Patent: Aug. 18, 2020

(54) METHOD OF PREDICTING/OPTIMIZING HYDROGEN SULFIDE SCAVENGING CAPACITY AND REDUCTION OF SCALE FORMATION

(71) Applicant: Schlumberger Norge AS, Hafrsfjord (NO)

(72) Inventors: Raquel Rodriguez Gonzalez, Harstad (NO); Anders Grinrod, Stavanger (NO)

(73) Assignee: Schlumberger Norge AS, Hafrsfjord (NO)

( * ) Notice: Subject to any disclaimer, the term of this patent is extended or adjusted under 35 U.S.C. 154(b) by 982 days.

(21) Appl. No.: 15/161,594

(22) Filed: May 23, 2016

(65) Prior Publication Data

US 2016/0289579 A1 Oct. 6, 2016

Related U.S. Application Data (62) Division of application No. 12/988,359, filed as application No. PCT/EP2009/054345 on Apr. 10, 2009, now Pat. No. 9,347,010.

(60) Provisional application No. 61/046,304, filed on Apr. 18, 2008.

(51) Int. Cl.
| | | |
|---|---|---|
| *B01D 53/14* | (2006.01) | |
| *C10L 3/10* | (2006.01) | |
| *G01N 33/00* | (2006.01) | |

(52) U.S. Cl.
CPC .......... *C10L 3/103* (2013.01); *B01D 53/1468* (2013.01); *B01D 53/1493* (2013.01); *C10L 3/10* (2013.01); *C10L 3/102* (2013.01); *G01N 33/0004* (2013.01); *B01D 2252/20436* (2013.01); *C10L 2290/141* (2013.01); *C10L 2290/545* (2013.01); *Y10T 436/147777* (2015.01)

(58) Field of Classification Search
None
See application file for complete search history.

(56) References Cited

U.S. PATENT DOCUMENTS

| | | |
|---|---|---|
| 4,680,127 A | 7/1987 | Edmondson |
| 4,978,512 A | 12/1990 | Dillon |
| 5,347,004 A | 9/1994 | Rivers et al. |
| 5,462,721 A | 10/1995 | Pounds et al. |
| 5,480,860 A | 1/1996 | Dillon |
| 5,554,349 A | 9/1996 | Rivers et al. |
| 5,688,478 A | 11/1997 | Pounds et al. |
| 5,744,024 A | 4/1998 | Sullivan, III et al. |
| 5,980,845 A | 11/1999 | Cherry |
| 6,063,346 A | 5/2000 | Luna |
| 6,242,618 B1 | 6/2001 | Forester et al. |
| 6,582,624 B2 | 6/2003 | Titley et al. |
| 6,663,841 B2 | 12/2003 | Salma et al. |
| 7,001,504 B2 | 2/2006 | Schoonover |
| 7,140,433 B2 | 11/2006 | Gatlin et al. |
| 7,211,665 B2 | 5/2007 | Gatlin |
| 2002/0182135 A1 | 12/2002 | Braga et al. |
| 2008/0056974 A1* | 3/2008 | Salma ..................... C02F 1/683 423/243.01 |

FOREIGN PATENT DOCUMENTS

| | | |
|---|---|---|
| CA | 2333794 A1 | 8/2002 |
| WO | 1998/50135 A1 | 11/1998 |
| WO | 2002/051968 A1 | 7/2002 |

OTHER PUBLICATIONS

Kenreck in Hydrocarbon Processing 93:73-6 (Year: 2014).*
"Dataplot: Tabulated Designs," Dataplot Statistical Engineering Division: National Institute of Standards and Technology retrieved on Oct. 16, 2010.
Bakke, et al. "Hydrolysis of 1, 3, 5—Tris (2 hydroxyethyl) hexahydro-s-triazine and Its Reaction with H2S," American Chemical Society; Ind. Eng. Chem Res, 2001, pp. 6051-6054.
Metzner, "New Developments of Thiocarbonyl Compounds and Sulfines in Organic Synthesis," Pure & Appl. Chem, vol. 68, No. 4, pp, 863-868, 1996.
Mixture Design Tutorial (Part 2—Optimization), Design-Expert 7 User's Guide; Apr. 12, 2006.
Nasr-El-Din, et al., "Investigation of Sulfide Scavengers in Well-Acidizing Fluids," 2002 SPE Production & Facilities, pp. 229-235.
Polasek, et al., "Selecting Amines for Sweetening Units," Bryan Research & Engineering, Inc. 2006.
Sprung, "A Summary of the Reactions of Aldehydes with Amines," Research Laboratory Company, Schenectady, New York, Aug. 1959, pp. 297-338.
International Search Report and Written Opinion for the equivalent International patent application PCT/EP2009/054345 dated Jan. 29, 2010.

* cited by examiner

*Primary Examiner* — Christopher M Gross

(57) ABSTRACT

A method of optimizing a hydrogen sulfide scavenger blend that includes selecting a hydrogen sulfide scavenger blend comprising at least two hydrogen sulfide scavengers; determining a scavenging capacity for the blend; modifying at least one blend parameter based on the determined scavenging capacity; redetermining the scavenging capacity for the modified blend; and selecting an optimized blend from the blend and the modified blend is disclosed.

7 Claims, 4 Drawing Sheets

METHOD OF PREDICTING/OPTIMIZING HYDROGEN SULFIDE SCAVENGING CAPACITY AND REDUCTION OF SCALE FORMATION

This application is a division of U.S. patent application Ser. No. 12/988,359 filed Feb. 2, 2011, which is a 371 National Phase of International Patent Application PCT/EP09/54345 filed Apr. 10, 2009, which claims priority to U.S. Provisional Application No. 61/046,304 filed Apr. 18, 2008. All three applications are incorporated herein by reference.

BACKGROUND OF INVENTION

Field of the Invention

Embodiments disclosed herein relate generally to hydrogen sulfide scavenger blends. In particular, embodiments disclosed herein relate generally to methods of predicting and/optimizing hydrogen sulfide scavenging capacity and reducing scale formation.

Background Art

Hydrocarbons, gases or liquid, are found in geologic formations located beneath the earth's surface. In particular, as obtained from beneath the earth's surface, raw natural gas is a mixture of gaseous hydrocarbons and non-hydrocarbon impurities, and thus, the undesirable impurities, including water, carbon dioxide, and sulfides (e.g., hydrogen sulfide). The presence of hydrogen sulfide or other sulfides is objectionable because such compounds may react with other hydrocarbons or fuel system components, are often highly corrosive and flammable, poisonous in very small concentrations, and emit highly noxious odors. However, sulfides are often present in crude oil and produced oil in addition to the gas phase.

Due to the offensive odor attributed to $H_2S$, $H_2S$-containing gas is often called "sour" gas, whereas treatments to reduce or remove $H_2S$ are often referred to as "sweetening." Substantial amounts of sour natural gas are currently being produced from natural gas wells, oil wells (as associated gas), and from natural gas storage reservoirs that have been infected with $H_2S$-producing bacteria. The presence of $H_2S$ in fuel and other gaseous streams has long been of concern for both the users and the producers of such gaseous streams. For example, in the case of natural gas, historically about 25% of the natural gas produced in the United States has been sour, that is, containing greater than about 4 ppm $H_2S$ (5.7 mg $H_2S/m^3$). In addition to the corrosive and other adverse effects that such impurities have upon equipment and processes with which such gaseous streams interact, noxious emissions are commonly produced from combustion of the natural gas as a result of oxidation of the hydrogen sulfide. The resulting sulfur oxides are a major contributor to air pollution and may have detrimental impact upon humans, animals, and plant life. Increasingly stringent federal and state regulations have accordingly been promulgated in an effort to reduce or eliminate sulfurous emissions, and a concomitant interest exists in efficiently removing from natural gas streams and the like the hydrogen sulfide that comprises a significant precursor of the emissions.

The sweetening or removal of $H_2S$ from petroleum or natural gas is only one example of where $H_2S$ level reduction must be performed. Other examples of where such technology is applied include the manufactured gas or coke-making industries, where coal gas contains unacceptable levels of $H_2S$ due to the distillation of bituminous coal having high levels of sulfur, the manufacture of water gas or synthesis gas where steam is passed over a bed of incandescent coke or coal that may contain sulfur, etc.

Regardless of the source of the liquid or gas stream from $H_2S$ is desired to be removed, there have been several mechanisms by which $H_2S$ is removed, including selective adsorption via absorbents and/or selective reaction of $H_2S$ with a reagent to produce a readily separable product. Such reagents are often termed $H_2S$ scavengers whereby the fluid stream is sweetened by the scavenging (removal or reduction) of $H_2S$ present in the sour gas (or other contaminated fluid streams). Hydrogen sulfide scavenging agents are most commonly applied through one of the following three methods: (1) batch application of liquid scavenging agents in a sparged tower contactor; (2) batch application of solid scavenging agents in a fixed-bed contactor; or (3) continuous direct injection of liquid scavenging agents. While gas streams must be free (or substantially free) of hydrogen sulfide prior to use, it is also preferable that such contaminants be removed or reduced prior to transport or processing in oil field equipment, pipelines, and refineries due to their corrosivity and flammability. Thus, a growing segment of the natural gas industry uses $H_2S$ scavenging processes at remote locations to remove low concentrations of $H_2S$ (usually less than about 300 ppm) from sub-quality natural gas.

Conventional $H_2S$ scavengers having included amines, aldehydes, alcohols, and reaction products of these materials. Many of such compounds are either too expensive for commercial use or evidence insufficient levels of hydrogen sulfide removal.

Accordingly, there exists a continuing need for developments in hydrogen sulfide removal from fluid streams contaminated with hydrogen sulfide.

SUMMARY OF INVENTION

In one aspect, embodiments disclosed herein relate to a method of optimizing a hydrogen sulfide scavenger blend that includes selecting a hydrogen sulfide scavenger blend comprising at least two hydrogen sulfide scavengers; determining a scavenging capacity for the blend; modifying at least one blend parameter based on the determined scavenging capacity; redetermining the scavenging capacity for the modified blend; and selecting an optimized blend from the blend and the modified blend.

In another aspect, embodiments disclosed herein relate to a method of selecting a hydrogen sulfide scavenger blend that includes defining at least one desired operational parameter; determining at least one blend comprising at least two hydrogen sulfide scavengers, wherein the at least one blend satisfies the at least one defined operational parameter; determining a scavenging capacity for the at least one blend; and selecting a blend based on the determined capacity.

In another aspect, embodiments disclosed herein relate to method of analyzing hydrogen sulfide scavenging capacity that includes determining hydrogen sulfide scavenging capacities for a plurality of hydrogen sulfide scavenger blends, each blend comprising defined blend parameters; generating a scavenging model comprising the defined blend parameters and the determined scavenging capacities; and determining the effects of the defined blend parameters on the scavenging capacity.

In yet another aspect, embodiments disclosed herein relate to a hydrogen sulfide blend that includes at least two hydrogen sulfide scavengers, at least one of the at least two hydrogen sulfide scavengers being a triazine, wherein the blend has a pH of less than 9.0.

Other aspects and advantages of the invention will be apparent from the following description and the appended claims.

DETAILED DESCRIPTION

In one aspect, embodiments disclosed herein relate to scavenging of fluid streams contaminated with hydrogen sulfide. Specifically, embodiments disclosed herein relate to the prediction and optimization of the scavenging capacity of hydrogen sulfide scavengers used to reduce or remove contaminating hydrogen sulfide from a fluid stream, such as a natural gas stream. Additionally, embodiments disclosed herein relate to the simultaneous optimization of scavenging capacity and scale minimization.

Hydrogen sulfide scavengers frequently used in the art have included oxygen- and nitrogen-containing compounds, reacting with hydrogen sulfide through substitution or addition reactions. There exists no limitation on the types of $H_2S$ scavengers that may be used in the methods and scavenging systems of the present disclosure; however, one skilled in the art would appreciate that among the wide variety of scavenging agents that may exist, some of the most frequently used include amines or aldehydes (or ketones), etc., and reaction products thereof. Among the most widely used scavengers, triazines, which are produced from the condensation of amines with formaldehyde, are formed as shown below in Eq. 1:

Eq. 1

Triazines react with $H_2S$ as shown in Eq. 2:

Eq. 2

(main product)

Trithiane (insoluble)

While triazines are effective at scavenging hydrogen sulfide, their primary drawbacks include the formation of the insoluble trithiane secondary byproduct and the release of amines during the reaction with $H_2S$, causing an increase in the pH of the resultant solution of spent triazine, thereby increasing the likelihood of scale formation such as calcium carbonate on the surfaces of equipment and at the injection point. However, decreasing the pH of the scavenger solution (to reduce scale formation) would result in a reduced scavenging capacity. Thus, a delicate balance between scavenging capacity and scale formation exists.

In accordance with embodiments of the present disclosure, statistical methods may be used to predict scavenging capacity and scale formation for blends of $H_2S$ scavengers so that an optimized blend of $H_2S$ scavengers may be obtained. Specifically, the inventors of the present disclosure have discovered by using a blend of multiple hydrogen sulfide scavengers and varying blend parameters (including pH), synergistic (and antagonistic) effects of the blends may be realized so that improvements in hydrogen sulfide scavenging and/or sufficient scavenging capacity at lower pHs may be achieved.

Response surface methodology (RSM) refers to a set of statistical methods that may be used to develop, improve, or optimize products, and may find particular use in situations where several factors (in the case of the $H_2S$ scavenger blends of the present disclosure, the proportions of individual component materials) influence one or more performance characteristics, or responses (e.g., scavenging capacity). RSM may be used to optimize one or more responses (e.g., scavenging capacity, pH), or to meet a given set of specifications (e.g., a minimum scavenging or an allowable range of pH values). There arc three general steps that comprise RSM: mixture approach/experiment design, modeling, and optimization.

Thus, in the present application, a $H_2S$ scavenger blend is a mixture of several components: various types of scavengers conventionally used alone. For a given set of scavengers forming a blend(s), the proportions of the components (as well as pH of individual components) directly influence the properties of the blend (including scavenging capacity and overall pH, which is indicative of likelihood of scale deposition).

The methodology of mixture design assumes that the sum of the component proportions in a mixture is 100% or 1. The use of mixture design allows for estimation of a property (i.e., scavenging capacity) starting from variations of the components. Thus, for a mixture having k number of components, the mixture of k components may optionally be transformed into k−1 independent mixture-related variables.

Figure 1:
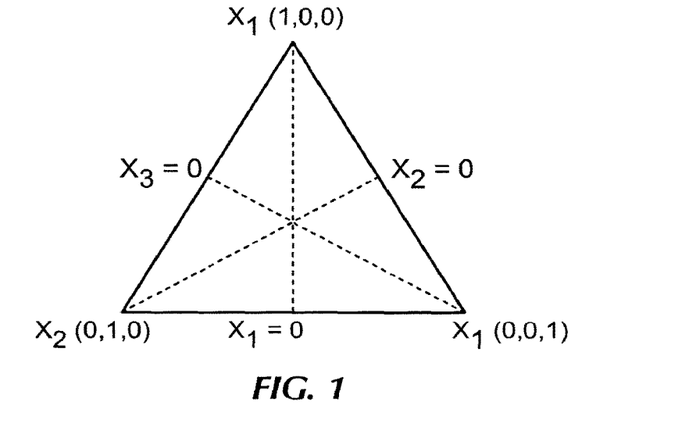
FIG. 1 shows a representative triangular simplex region for a three-component mixture experiment.

For illustrative purposes, for a mixture of three components ($x_1$, $x_2$, and $x_3$), the volume fraction of the components sum to 1, and the region defined by this constraint is a regular triangle, shown in FIG. 1. The axis for each component $x_i$ extends from the vertex ($x_i=1$), representing the pure component, to the midpoint of the opposite side of the triangle ($x_i=0$). The point where the three axis intersect, with coordinates (1/3, 1/3, 1/3) is called the centroid.

All responses (properties) of interest would be measured for each mixture in the design and modeled as a function of the three components using polynomial functions. A linear polynomial model (for a three component mixture) for a response y is:

$$y=b_0^*+b_1^*x_1+b_2^*x_2+b_3^*x_3+e \qquad \text{Eq. 3,}$$

where $b_i^*$ are constants and e, the random error term, represents the combined effects of all variables not included in the model. For a mixture experiment where $x_1+x_2+x_3=1$ (i.e., $b_0^*=b_0^*(x_1+x_2+x_3)$), we can multiply $b_0^*$ with ($x_1+x_2+x_3$) to give:

$$y=b_0^*x_1+b_0^*x_2+b_0^*x_3+b_1^*x_1+b_2^*x_2+b_3^*x_3+e \qquad \text{Eq. 4}$$

which can be rewritten as:

$$y=(b_0^*+b_1^*)x_1+(b_0^*+b_2^*)x_2+(b_0^*+b_3^*)x_3+e \qquad \text{Eq. 5}$$

giving:

$$y=b_1x_1+b_2x_2+b_3x_3+e \text{ (where } b_i=b_0^*+b_i^*\text{)} \qquad \text{Eq. 6.}$$

This equation is referred to as the Scheffé linear mixture polynomial for three components.

Similarly, to account for curvature in a model, a quadratic polynomial, also including terms representing the interaction $b_{ij}$ between components (for example, any synergistic and antagonistic interactions between multiple scavenger components that may effect scavenging), for a response y is:

$$y=b_0^*+b_1^*x_1+b_2^*x_2+b_3^*x_3+b_{12}^*x_1x_2+b_{13}^*x_1x_3+\\b_{23}^*x_2x_3+b_{11}^*x_1^2+b_{22}^*x_2^2+b_{33}^*x_3^2+e \qquad \text{Eq. 7,}$$

considering that $$x_i^2 = x_i\left(1 - \sum_{\substack{j=1\\j\neq i}}^{q} x_j\right),$$

the polynomial can be reparameterized as:

$$y=b_1x_1+b_2x_2+b_3x_3+b_{12}x_1x_2+b_{13}x_1x_3+b_{23}x_2x_3+e \qquad \text{Eq. 8}$$

However, one skilled in the art would appreciate that models such as cubic models also exist. Further, selection of the appropriate model among the various types of models may be based on fitting the data to the models using analysis of variance and least squares techniques, for example. In addition to selecting a model, selection of a design may also be made. One skilled in the art would appreciate that selection of a design is largely based on the type of model selected. For example, optimal designs operate by choosing an "optimal" property, i.e., D-optimal designs focus on minimizing the variance associated with the b-coefficients for a model where as I-optimal designs focus on finding the best predictions from a model by putting fewer design points at the extremes of the design space. However, other designs such as factorial designs, fractional factorial, central composite designs, face-centered cubic designs, and uniform shell designs may also be used. Further, one skilled in the art would appreciate that in generating a model, a first design, such as a D-optimal point design, may be used to screen a number of blends, and then an I-optimal point design may then be used in an attempt to improve the predictive quality of the models.

When appropriate models have been established, several responses can be optimized simultaneously. Optimization may be performed using mathematical (numerical) or graphical (contour plot) approaches. Numerical optimization requires defining an objective function (called a desirability or score function) that reflects the levels of each response in terms of minimum (zero) to maximum (one) desirability. As an alternative to rigorous numerical methods, desirability may be evaluated by superimposing a grid of points at equal spacing over the experimental region and evaluating desirability at each point. The point(s) of maximum desirability may be found by sorting the results or by creating contour plots of desirability over the grid area.

Further, once a model has been generated and/or effects of various blend parameters on scavenging capacity are determined, any portion of the (or all) generated data or model may be stored in a library (i.e., database) for future use.

The following example is used to better illustrate the way in which such methods may be used to predict scavenging capacity and select an optimized blend of hydrogen sulfide scavengers. However, this example is only illustrative, and no limitation should exist on the scope of the present disclosure.

In the example, various ratios of formulations of 1,3,5-tris(2-hydroxyethyl)hexahydro-1,3,5-triazine (Component A) at a pH of 9.83 (pH achieved by acid addition), N,N'-di(hydroxymethyl)ethylenediamine (Component B) at a pH of 7.96, 1,3,5-trimethylhexahydro-1,3,5-triazine (Component C) at a pH of 9.42, and glyoxal (Component D) at a pH of 2.84, were tested to determine whether each of the scavengers were more efficient as $H_2S$ scavengers alone or when combined with each other. Thus, various combinations and ratios were tested, and the results were submitted to statistical experimental design and multivariate modeling. Thus, in accordance with embodiments of the present disclosure, statistical mixture designs may be used to optimize the proportions (and identity) of components that make up an $H_2S$ scavenger blend, as well as to identify interaction effects (synergistic or antagonistic) that may play an important part in optimizing scavenger blends.

In this example, the mixture design uses a quadratic model with D-optimal point exchange, with k={no. of components}=4 (components A-D) and n_ {no. of runs}=15. Components A-C were varied between 0 mL and 25 mL of each component, whereas component D was varied between 0 and 7.5 mL Each of the blends had a total component volume of 25 mL The blends tested are shown below in Table 1:

TABLE 1

| | Blend Components | | | | | Responses | |
| --- | --- | --- | --- | --- | --- | --- | --- |
| | | | | | | Scavenging Capacity ($y_1$) ($H_2S$ drop after | $y_2$ (1/$y_1$) |
| Sample | A (mL) | B (mL) | C (mL) | D (mL) | pH | 1 min) (ppm) | (ppm$^{-1}$) |
| 1 | 17.5 | — | — | 7.5 | 7.6 | 26 | 0.038 |
| 2 | — | 12.5 | 12.5 | — | 9.6 | 35 | 0.029 |
| 3 | 12.5 | — | 12.5 | — | 9.77 | 40 | 0.025 |
| 4 | — | — | 25 | — | 9.42 | 25 | 0.040 |
| 5 | 25 | — | — | — | 9.83 | 32 | 0.031 |
| 6 | 12.5 | 12.5 | — | — | 9.28 | 30 | 0.033 |
| 7 | 10.625 | 10.625 | — | 3.75 | 5.89 | 7 | 0.143 |
| 8 | — | 8.75 | 8.75 | 7.5 | 5.31 | 4 | 0.250 |
| 9 | 3.542 | 16.042 | 3.542 | 1.875 | 7.39 | 12 | 0.83 |
| 10 | — | 17.5 | — | 7.5 | 2.36 | 2 | 0.500 |
| 11 | — | — | 17.5 | 7.5 | 8.68 | 35 | 0.029 |
| 12 | 16.042 | 3.542 | 3.542 | 1.875 | 7.87 | 34 | 0.029 |
| 13 | 8.333 | 8.333 | 8.333 | — | 9.49 | 39 | 0.026 |
| 14 | — | 25 | — | — | 7.96 | 15 | 0.067 |
| 15 | 8.75 | — | 8.75 | 7.5 | 7.6 | 27 | 0.037 |

A total of 15 blends (Samples 1-15) comprise the blend matrix in Table 1 above. For each blend, the scavenging capacity ($y_1$) [ppm] and 1/scavenging capacity ($y_2$) [ppm$^{-1}$], both measured after one minute of reaction time, were measured. The reactions were carried out at 20° C. for 10 minutes using a dose rate of 10 ppm of $H_2S$ scavenger for every 1 ppm of $H_2S$. The scavenging capacity of each product versus time is shown in FIG. 1. The course of each reaction was monitored by a Dräger Pac III-$H_2S$ measuring device.

Quadratic modeling using a D-optimal point design allowed for the estimation of the regression coefficients $b_i$ representing the main effect for the components A-D, and regression coefficients $b_{ij}$ representing the interaction effects between components A-D (A×B, A×C, A×D, B×C, B×D, C×D). The final model matrix was then submitted to multivariate modeling, to provide a quadratic model for the response 1/scavenging capacity given in Eq. 9 below.

$$y_2 = b_1A + b_2B + b_3C + b_4D + b_{12}(A*B) + b_{13}(A*C) + b_{14}(A*D) + b_{23}(B*C) + b_{24}(B*D) + b_{34}(C*D) \quad \text{Eq. 9,}$$

which for the data in Table 1, may be estimated as:

$$y_2 = 0.032A + 0.061B + 0.041C + 1.410D - 0.040(A*B) - 0.030(A*C) - 1.910(A*D) - 0.120(B*C) + 0.160(B*D) - 2.000(C*D) \quad \text{Eq. 10.}$$

Figure 4A:
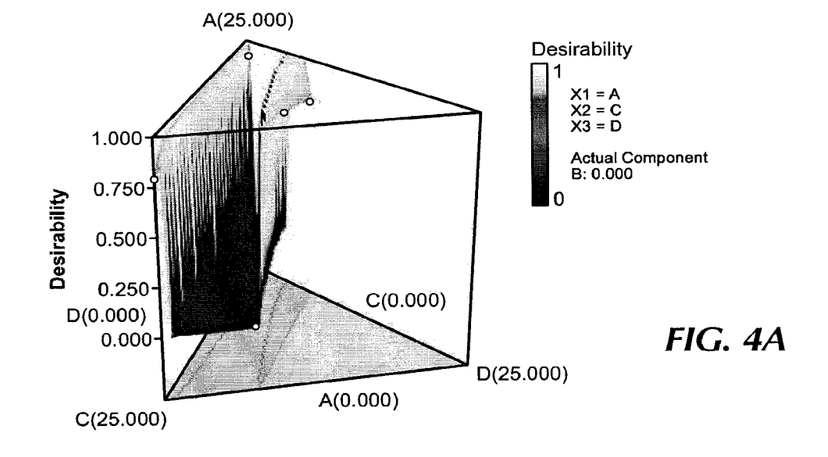
FIGS. 4A-C show mixture response-surface plots for various blends.
Figure 4B:
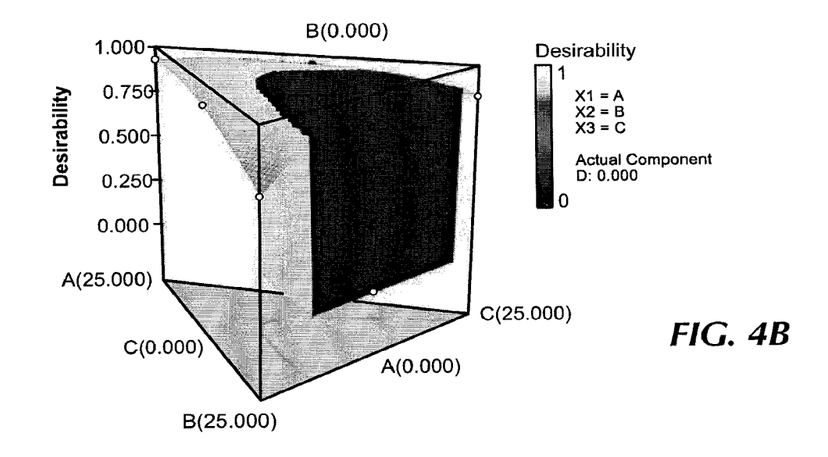
Figure 4C:
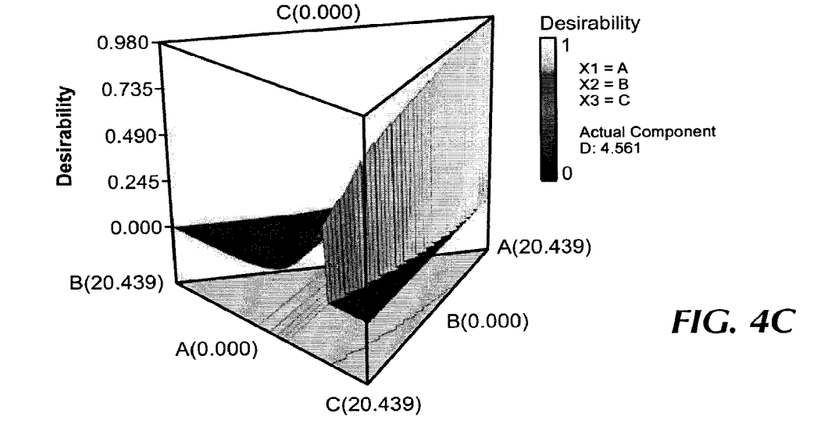

The estimated regression coefficients for the model were plotted in a cumulative normal distribution plot showing that $b_4$, $b_{14}$, $b_{23}$, $b_{24}$, and $b_{34}$ were statistically significant and thus contribute to the explanation of the variation in the response $y_2$. The quadratic model of Eq. 10 was to estimate two- and three-dimensional response surface plots for the two-, three- and four-component interactions, as shown in FIGS. 3 and 4. The model in Eq. 10 may also be used to determine those parameters that are important for increasing the $H_2S$ scavenging capacity after 1 min. Thus, it was determined that among the linear blending coefficients ($b_i$), the coefficient for Component D, glyoxal, ($b_4$) is much larger than those for Components A-C, which all have more similar values.

The plots predicted that, in order to obtain high $H_2S$ scavenging, blends containing N,N'-di(hydroxymethyl)ethylenediamine must be in the absence of glyoxal due to the strong antagonistic interactions between the two components. The likely explanation for this effect may be explained by the likelihood for aldehydes such as glyoxal to react with alcohols in excess in the presence of an acid ($H^+HS^-$) to give acetals. This side reaction may occur faster than the reaction between hydrogen sulfide with the alkanolamine, affecting the scavenging capacity of both the alkanolamine and the aldehyde. Thus, the presumed acetal formation appears to have negative effects in terms of $H_2S$ scavenging capacity. However, the acetal formation does not seem to occur in the blends containing glyoxal with the 1,3,5-trimethylhexahydro-1,3,5-triazine, more probably due to steric hindrance. Further, glyoxal may also react with amines released from triazines after reaction with $H_2S$, to further act as an $H_2S$ scavenger and increase the total scavenging effect of the blend.

Figure 2:
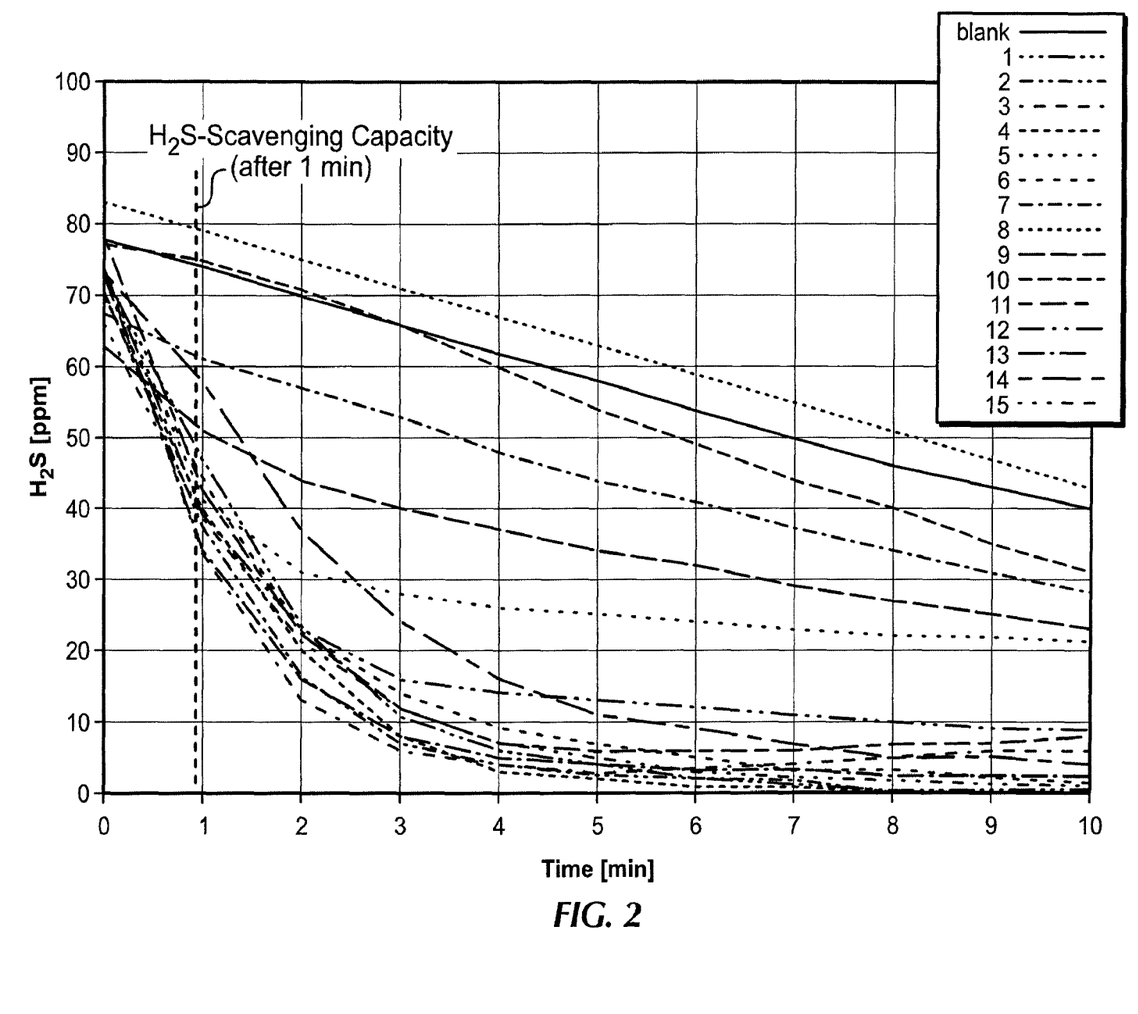
FIG. 2 shows a hydrogen sulfide scavenging capacity versus time plot for various hydrogen sulfide scavenging blends.
Figure 3A:
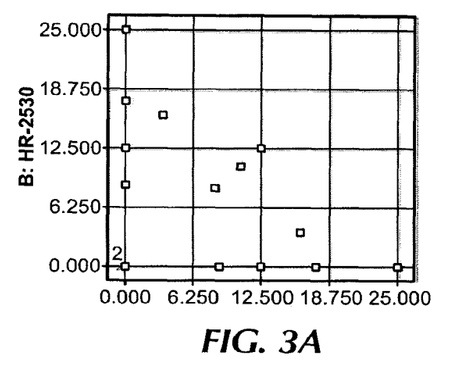
FIGS. 3A-F show mixture contour plots of the two-factor interaction effects for various blends.
Figure 3B:
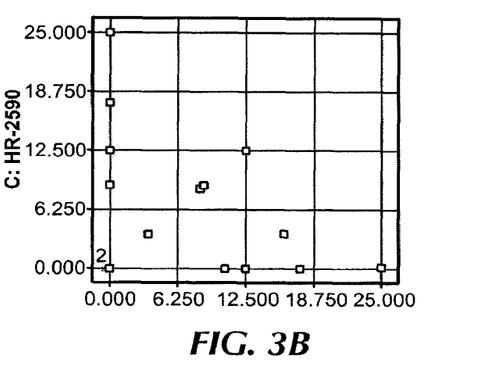
Figure 3C:
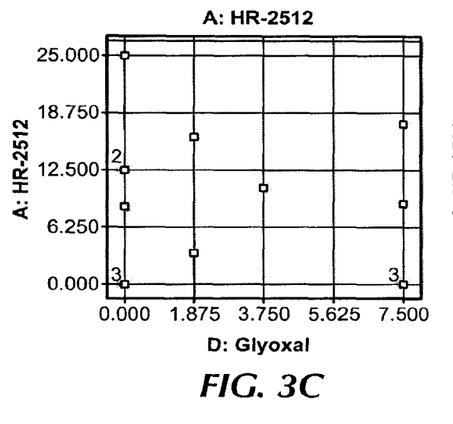
Figure 3D:
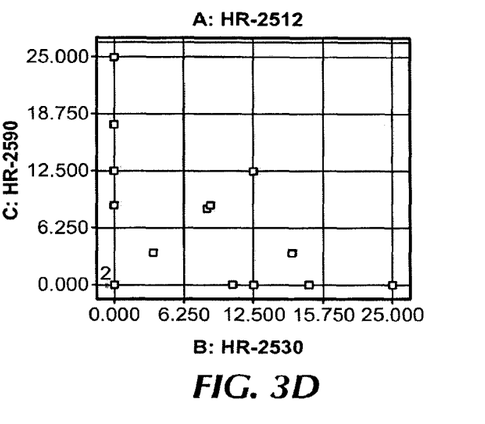
Figure 3E:
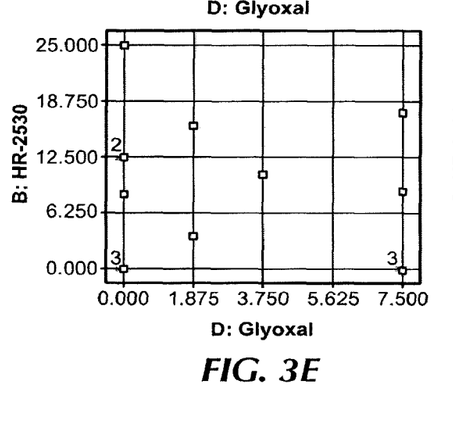
Figure 3F:
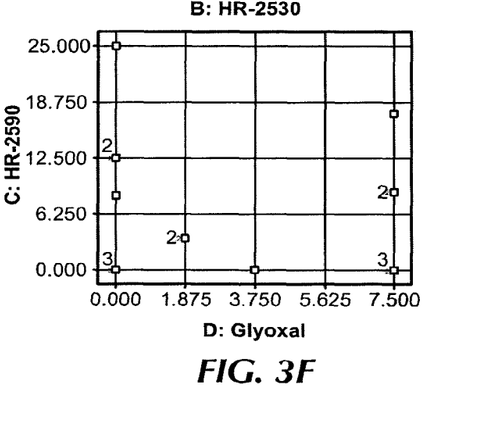

Another observation was that the alkanolamine behaves better in combinations with the triazines than alone. In all cases, combinations of the triazines and alkanolamine provided larger $H_2S$ scavenging than by using single component blends. The presence of glyoxal in those blends can be detrimental to the scavenging capacity when the alkanolamine is present. Of all blends tested, the 1:1 blend of the two triazines and the 1:1:1 blend of the two triazines with the alkanolamine provided the largest scavenging effects after one minute. Among the two-component interaction coefficients in Eq. 4, two are the most important: $b_{14}$ (−1.910) and $b_{34}$ (−2.000); consequently, it is evident from this that control of the proportions of the triazines and glyoxal in the blends is important to optimize scavenging capacity. From the response surface projections in FIGS. 2 and 3, blend conditions were selected to represent optimized blends. Based on the response surface projections and mathematical approaches, the maximum scavenging value after one minute ($y_1 \approx 71$-78 ppm, and $y_2 \approx 0.014$-0.013 ppm$^{-1}$) was predicted to occur for blends comprising 35-70% Component A; 0-35% Component C, and 20-24% Component D.

Figure 5:
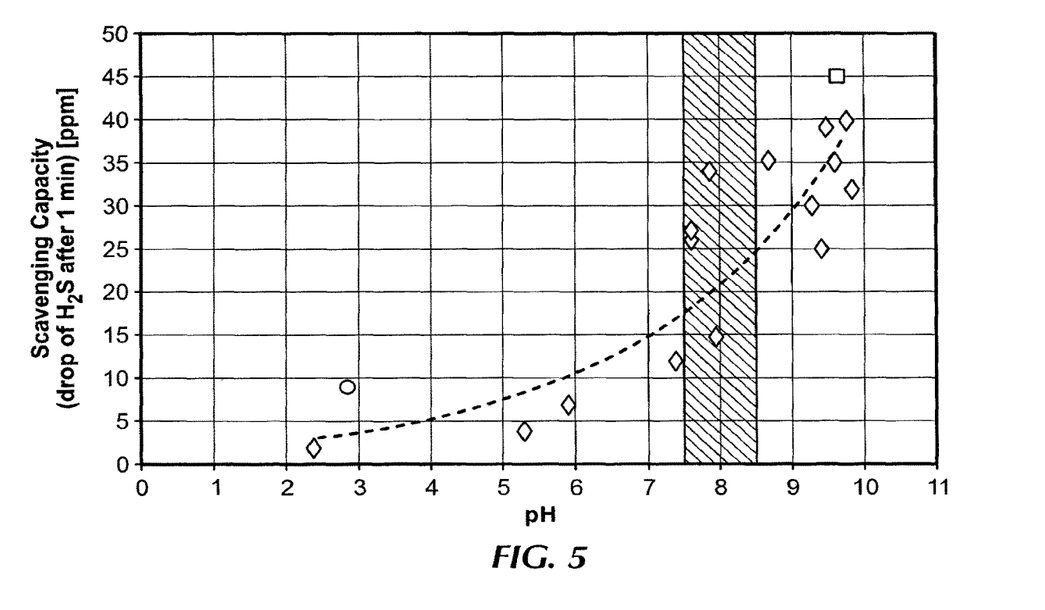
FIG. 5 shows a hydrogen sulfide scavenging capacity versus pH plot for various hydrogen sulfide scavenging blends.

The scavenging capacity of samples 1-15 and 19-20 were plotted with respect to pH, as shown in FIG. 5. From FIG. 5, it is evident that blends with a too low pH (≤7.5) show low to minimum $H_2S$ scavenging effects. Further, blends with the highest pH values are the most effective scavengers, but they have a high pH, undesirably increasing scale deposition. Thus, it was determined that blends having pH values less than 9, and preferably ranging from 7.5 to 8.5 may allow for optimization of $H_2S$ scavenging without significant $CaCO_3$ or other scale deposition. In a particular embodiment, a pH value ranging between 7.6 and 8.3 may be particularly desirable. However, depending on the requirements of a particular system, other pH ranges may also be used.

However, as discussed above, mineral scale deposition (predominantly $CaCO_3$ deposition) occurs because triazine-based scavengers increase the pH and consequently the scaling potential. Components A-D all have reduced pH values (9.83, 7.96, 9.42, and 2.84, respectively) than that of typical hydrogen sulfide scavengers (greater than 11). Conventional hydrogen sulfide scavengers possess higher pH values because reduced alkalinity reduces scavenging capacity. However, the inventors of the present disclosure have balanced the scavenging capacity with scale deposition (which begins to occur when the pH of the system exceeds 8.30). Reduction of pH may be achieved by blending an acid with the scavenger blend (or components) or by using a scavenger component having an inherently lower pH such as glyoxal or formulated with acid to achieve a lower pH. Further, while this illustrative example does not include optimization of pH, it is also within the scope of the present disclosure that an acid component may be used as a blend component/parameter that may be optimized using the statistical design methods disclosed herein.

The blends for optimization experiments are listed in Table 2 below. Also listed in Table 2 is the comparative sample of glyoxal alone (40% solution in water).

|  | Blend Components | | | | | Responses | |
| --- | --- | --- | --- | --- | --- | --- | --- |
|  |  |  |  |  |  | Scavenging Capacity $(y_1)$ ($H_2S$ drop after |  |
| Sample | A (mL) | B (mL) | C (mL) | D (mL) | pH | 1 min) (ppm) | $y_2$ ($1/y_1$) (ppm$^{-1}$) |
| 16 | 13.42 | — | 6.045 | 5.536 | 8.34 | — | — |
| 17 | 17.56 | — | 1.547 | 5.893 | 8.08 | — | — |
| 18 | 20.041 | — | — | 4.959 | 8.24 | — | — |
| 19 | 10.711 | 5.373 | 8.916 | — | 9.65 | 45 | 0.022 |
| 20 (Comp) | — | — | — | 25.0 | 2.84 | 9 | 0.111 |

From this example modeling, optimal blends (with a balance of scavenging capacity and pH to minimize scale deposition) were predicted to occur for blends comprising 35-70% Component A; 0-35% Component C, and 20-24% Component D, having pH values less than 9, and preferably ranging from 7.5 to 8.5. Based on the quadratic model, a solution of 43% Component A: 21% Component B: 36% Component C (sample 19) was also indicated as optimal to maximize the $H_2S$ scavenging capacity $y_1$. The predictive value of $y_1$ (42 ppm) for sample 9 is indeed close to the observed value of 45 ppm reported in Table 2. This result confirms the predictive capacity of the quadratic model in Equation 10.

However, in addition to generation of a scavenging model and determining the effects of blend parameters (component type, amount, pH, etc.) on scavenging capacity, methods of the present disclosure also relate to the use of models to select or optimize a blend. For example, in one embodiment, a hydrogen sulfide scavenger blend may be optimized. In such an embodiment, an initial blend (i.e., at least two scavengers contained therein) may be selected, including a blend selected from a library, or from desired blend parameters. Determination of a predicted scavenging capacity may be achieved for the particular blend such as by using a scavenging model that has analyzed/determined the effects of various blend parameters (as well as possible multi-component interactions) on the scavenging capacity. Then, based on the determined scavenging capacity for the particular blend that was initially selected, at least one blend parameter (such as type, amount, pH) may be modified, and the scavenging capacity for the modified blend may be re-determined. The scavenging capacity and/or pH may be compared for the initial and modified blend, and an optimized blend may be selected therefrom. One skilled in the art would appreciate that an "optimized blend" may be a blend having properties or characteristics desired for a particular application and does not necessarily mean the highest scavenging capacity. Rather, an optimized blend may be a blend that possesses at least a minimum scavenging capacity with a maximum pH requirement. Further, one skilled in the art would appreciate that while only two blends are used in the selection of the optimized blend, any number of iterations of modifying a blend parameter may be made and any number of blends may be used in the selection process for the optimized blend.

However, in another embodiment of the present disclosure, an initial operational parameter may be defined, or predefined, depending on the requirements of a particular injection system, including for example solubility characteristics that may be required depending on where the injection occurs. Specifically, one skilled in the art would appreciate the reaction products of the two types of triazines used in the example above have different solubility characteristics. The triazine formed from methyl amine is more oil soluble whereas the reaction product of ethanolamine is more water-soluble. Thus, for systems where the triazine is injected into the gas stream downstream of a three-phase separator, but upstream of a glycol dehydration unity, the ultimate fate of the reaction products from the two chemicals will be different: the water-soluble components will concentrate in the glycol system whereas the oil soluble components will be returned to the main separator train with the light hydrocarbon fractions. Further, one skilled in the art would appreciate that the volatility among the various scavenger chemistries may vary, and thus, depending on the temperatures and/or pressures expected in the injection system, chemistries with sufficient stability (less volatile) may be preferred for use in a blend.

In addition to type of chemistry selected, pH (and scale deposition prevention), minimum scavenging, injection system parameters including injection point, pressures, temperature, price, etc., may represent alternative types of operational requirements for a particular injection system. Further, one skilled in the art would appreciate that there is no limit on the type and number of operational limitations that may be used as an initial defining parameter which may be used to determine an initial set of blends that meet such defined requirements.

Once the various blends that satisfy the defined operational parameters are determined, the scavenging capacity for each blend may be determined, such as by using a scavenging model that has analyzed/determined the effects of various blend parameters (as well as possible multi-component interactions) on the scavenging capacity and/or selecting a blend from a library of blends. From the determined or predicted scavenging capacity, a blend determined to be suitable for the particular application may be determined, such as a blend that satisfies the operational parameters, but also possesses more than sufficient scavenging at a pH that will not induce significant scale formation.

Further, once a blend is selected or an optimized blend is obtained, the hydrogen sulfide scavenger blend may be brought into contact with a liquid and/or gaseous stream of hydrocarbons having hydrogen sulfide contained therein. One skilled in the art would appreciate that the methods and blends of the present disclosure are applicable to a wide variety of fluid streams, including liquefied petroleum gas as well as crude oil and petroleum residual fuel, heating oil, etc., as well as gaseous hydrocarbon streams. For instance, the scavenger may be contacted with wet or dry gaseous mixtures of hydrogen sulfide and hydrocarbon vapors, such as is found in natural gas or obtained in the drilling, removal from the ground, storage, transport, and processing of crude oil.

Further, there is no limitation on the way in which the $H_2S$ scavengers may be added to a $H_2S$-contaminated stream, i.e., how the scavenger is contacted with the stream. Conventional direct-injection $H_2S$ scavenging uses an open pipeline as a contactor. In these applications, $H_2S$ scavenging agents may be injected into the gas stream where $H_2S$ is absorbed into the solution and reacted to form byproducts which are subsequently removed from the natural gas stream and discarded. An alternative method for direct-injection $H_2S$ scavenging involves the forcing of a liquid jet of $H_2S$ scavenging agent through a small opening under high pressure, such as an atomizing nozzle, thereby causing the jet to break apart into small droplets.

Further, one skilled in the art would appreciate that depending on the type of injection system, it may be desirable to ensure sufficient mixing of the scavenger with the fluid stream, to provide direct contact between the scavenger and $H_2S$ so that reaction between the two compounds may occur. Thus, for example, to achieve sufficient mixing, injection may take place in a turbulent flow system. Alternatively, in non-turbulent flow systems, a static mixer or atomizing injection nozzles may be used.

Additionally, while various specific chemistries have been described above, there exists no limitation on the number or types of scavenger chemistries that may be used in accordance with the blends of the present disclosure. For example, while 1,3,5-trimethyl-hexahydro-1,3,5-triazine and 1,3,5-tris(2-hydroxyethyl)hexahydro-1,3,5-triazine have been described as being types of triazines suitable for use in the blends and methods of the present disclosure, it is also within the scope of the present disclosure that other triazines may also be used, including, for example, triazines formed from the reaction of formaldehyde with various amines including methylamine, ethylamine, n-propylamine, t-butylamine, ethanolamine, propanolamine, etc., as well as mixtures thereof. Further, in addition to variation among the types of triazine scavengers that may be used, there also exists no limitation on the types of other scavengers that may be used, including other aldehydes, alkylamines, as well as other organic or inorganic scavengers. Additionally, one skilled in the art would appreciate that any organic or inorganic acids may be used as acid components or pH modifiers.

Advantageously, embodiments of the present disclosure may provide for at least one of the following. Methods of the present disclosure may provide for methods for predicting hydrogen sulfide scavenging capacity and pH of a blend. By providing means for analyzing scavenging capacity and pH, a hydrogen sulfide scavenging blend may be used that simultaneously provides for optimization of scavenging capacity without risk of complications due to scale deposition. Further, the methods allow for determination of synergistic/antagonistic interactions between multiple components in a blend so that a blend with the highest scavenging capacity and lowest risk of scale formation may be achieved. Further, the methods may also allow for optimization of blends by modifying blend parameters in view of predicted effects as well as selection of a blend having desirable scavenging capacity/pH in view of predefined operational constraints.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A method of selecting a hydrogen sulfide scavenger blend, comprising:
   generating a model by submitting experimental test results associated with a plurality of blends to statistical experimental design and multivariate modeling, wherein the statistical experimental design comprises one or more optimal designs selected from D-optimal designs, I-optimal designs, factorial designs, fractional factorial designs, central composite designs, face-centered cubic designs, and uniform shell designs;
   storing a portion or all of the generated model in a library of a database;
   defining at least one desired operational parameter;
   determining at least one blend by selecting the at least one blend from the plurality of blends, wherein the at least one blend comprises at least two hydrogen sulfide scavengers and satisfies the defined at least one desired operational parameter;
   determining a scavenging capacity for the determined at least one blend based on the generated model; and
   selecting a blend based on the determined scavenging capacity.

2. The method of claim 1, further comprising:
   determining a pH for the at least one blend; and
   selecting a blend based on the determined pH.

3. The method of claim 1, wherein the generated model is a scavenging model and the determining the scavenging capacity comprises predicting the scavenging capacity from the scavenging model.

4. The method of claim 1, wherein the at least one desired operational parameter comprises at least one of scavenger chemistry, maximum pH, and minimum capacity.

5. The method of claim 1, wherein at least one of the at least two hydrogen sulfide scavengers comprises a triazine.

6. The method of claim 1, further comprising:
   injecting the selected blend into a hydrocarbon stream.

7. A method of selecting a hydrogen sulfide scavenger blend, comprising:

generating a scavenging model by submitting experimental test results associated with a plurality of blends to statistical experimental design and multivariate modeling;

storing a portion or all of the generated scavenging model in a library of a database;

defining at least one desired operational parameter;

determining at least one blend by selecting the at least one blend from the plurality of blends, wherein the at least one blend comprises at least two hydrogen sulfide scavengers and satisfies the defined at least one desired operational parameter;

determining a scavenging capacity for the determined at least one blend by predicting the scavenging capacity from the generated scavenging model; and selecting a blend based on the determined scavenging capacity.

* * * * *